United States Patent
Cronin

(10) Patent No.: US 7,955,368 B2
(45) Date of Patent: Jun. 7, 2011

(54) RADIATION APPLICATOR

(76) Inventor: Nigel Cronin, Bath (GB)

( * ) Notice: Subject to any disclaimer, the term of this patent is extended or adjusted under 35 U.S.C. 154(b) by 0 days.

(21) Appl. No.: 12/212,234

(22) Filed: Sep. 17, 2008

(65) Prior Publication Data

US 2009/0054888 A1  Feb. 26, 2009

Related U.S. Application Data

(60) Continuation of application No. 11/513,885, filed on Aug. 31, 2006, now abandoned, which is a division of application No. 09/914,375, filed on Jan. 15, 2002, now Pat. No. 7,118,590, which is a division of application No. PCT/GB00/00682, filed on Feb. 25, 2000.

(30) Foreign Application Priority Data

Feb. 25, 1999 (GB) .................................. 9904373.9

(51) Int. Cl.
*A61N 1/06* (2006.01)

(52) U.S. Cl. ......................................... 607/105; 606/33

(58) Field of Classification Search .................... 606/33, 606/41; 607/96, 98–101, 154–156
See application file for complete search history.

(56) References Cited

U.S. PATENT DOCUMENTS 5,471,222 A * 11/1995 Du ................................ 343/713
6,047,216 A *  4/2000 Carl et al. ..................... 607/101

FOREIGN PATENT DOCUMENTS

| WO | WO 93/20768 | 10/1993 |
|----|-------------|---------|
| WO | WO 99/56643 | 11/1999 |

* cited by examiner

*Primary Examiner* — Ahmed M Farah
*Assistant Examiner* — Aaron Roane
(74) *Attorney, Agent, or Firm* — Eugene M. Commings, P.C.

(57) ABSTRACT

This invention provides an elongate microwave radiator for insertion into a living body to treat tissue at a predetermined operating frequency. The radiator defines a monopole antenna at its tip. The monopole antenna includes a dielectric material surrounding the monopole. The dielectric material is configured to act as a resonator at the predetermined operating frequency, and encompasses generally the whole of a near-field radiation emitted by the monopole. In an illustrative embodiment, the dielectric material extends from the antenna a distance determined in accordance with the wavelength of the radiation in the dielectric.

2 Claims, 2 Drawing Sheets

RADIATION APPLICATOR

RELATED APPLICATIONS

This application is a continuation of prior application Ser. No. 11/513,885, filed Aug. 31, 2006 now abandoned, which is a divisional of U.S. patent application Ser. No. 09/914,375, filed on Jan. 15, 2002, now U.S. Pat. No. 7,118,590 and claims the benefit of International Application No. PCT/GB00/00682, filed on Feb. 25, 2000, and claims the benefit of GB Application No. 9904373.9, filed Feb. 25, 1999, entitled RADIATION APPLICATOR by Nigel Cronin.

BACKGROUND OF THE INVENTION

1. Field of the Invention

This invention relates to microwave radiators and, in particular, to microwave ablation devices.

2. Background Information

A known microwave radiator, used for microwave ablation of tissue, compromises a microwave generator operatively coupled to an elongated waveguide for conveying the microwaves to the ablation site. The waveguide is sufficiently thin to be inserted into the body and contains a core dielectric material which enables efficient transmission of microwaves through the waveguide. At the emission end of the waveguide, the dielectric core protrudes and provides a radiating tip for coupling microwaves into surrounding tissue. An object of the invention is to provide an improved radiation applicator.

According to one aspect, the invention includes an elongate microwave radiator for insertion into a living body to treat biological tissue at a predetermined operating frequency, the radiator comprising a monopole at its tip and dielectric material surrounding the monopole; characterized in that said dielectric material is adapted so that it acts as a resonator at said predetermined operating frequency, and encompasses generally the whole of the near-field radiation emitted by the monopole.

The invention is based on an appreciation of the fact that a monopole antenna generates a near-field, and that the near-field contains large field amplitudes which exist quasi-statically in the local region of the monopole and do not radiate energy. In a normal communications antenna, this local region is air-filled and these near-field amplitudes have no effect except to contribute reactance to the antenna impedance. However, in a medical application, if the near-field region contains biological matter, which is highly lossy, the near-field amplitudes will generate heat. Because of the high amplitudes and small volume of the near-field region, much heat can be generated in the near-field region, which reduces the energy in the far-field. Field penetration is therefore reduced, and local charring in the near-field region becomes a limiting factor in the power that can be input to the antenna.

The dielectric body according to the invention serves to provide a low loss environment to encompass the near field region so that more power is transmitted to the biological matter in the far-field region.

The extent of the near-field is determined by the wavelength $\lambda$ of the radiation in the dielectric and the length L of the monopole according to the relationship $2L^2/\lambda$. The extent of the near-field therefore is proportional to $\lambda$, and it is possible to reduce the extent of the near-field region by increasing, the dielectric constant of the body to reduce the wavelength of the radiation within it. The overall external dimension of the device can therefore be reduced for insertion into a living body. A higher dielectric constant will also accommodate the use of lower frequency radiation, which would otherwise increase the wavelength and the extent of the near-field; the lower frequency radiation being beneficial in increasing radiation penetration into the far-field.

A monopole antenna, for good impedance matching, has L generally equal to $\lambda/2$. By substitution in the above relationship, the extent of the near-field is then equal to $\lambda/2$, and this determines the minimum extent of the dielectric material. Furthermore, a $\lambda/2$ dimension for the dielectric material is consistent with its operation as a resonator to ensure that the radiator is effective in transmitting radiation at the required power levels for the treatment of biological material.

In one embodiment of the invention, the dielectric body comprises a cylindrical shape with the monopole extending axially along its center. A radiator of this kind can be designed with a minimum radius for insertion into biological matter such as a liver, and will create an annular radiation field around it. A pointed tip may be provided at the free end of the dielectric body to assist penetration of biological matter.

As the dielectric constant is increased, it may exceed that of the biological matter, which can lead to total internal reflection of radiation within the dielectric and a consequent reduction in transmitted radiation. In order to overcome this problem, the dielectric body is formed so that the dielectric constant at its core is higher than that at its outer periphery, the latter having a value intermediate that of the core and the biological matter. Thus, the dielectric constant at the core may be higher than that of the surrounding biological matter so as to help reduce the overall diameter of the radiator. The different dielectric constants may correspond to different layers of dielectric, each with a different dielectric constant, or may correspond to different levels in a dielectric in which the dielectric constant varies throughout the depth.

According to another aspect, the invention includes an elongate microwave radiator for insertion into a living body to treat biological tissue at predetermined operating frequency, the radiator comprising a monopole at its tip and dielectric material surrounding and extending beyond the monopole; characterized in that said dielectric material terminates in a rounded tip portion and is adapted so that it acts as a resonator at said predetermined operating frequency and enhances transmission of radiation in the forward direction of insertion.

Preferably, the tip portion is generally hemispherical and has a radius generally equal to half a wavelength of the radiation.

The radiator may further comprise a coaxial conductor (preferably packed with a dielectric) which supplies radiation to the monopole antenna from a radiation generator. Preferably, the monopole then comprises an exposed length of the central conductor of the coaxial conductor at its distal end. Preferably, the exposed length of the central conductor providing the monopole is generally half the wavelength of the radiation in the dielectric. The coaxial conductor may be rigid or flexible cable.

Preferably, the dielectric material has a dielectric constant, or relative permittivity, such that the length of the monopole is reduced. Advantageously, there can be a transformer between the coaxial conductor and the dielectric monopole to reduce reflection of radiation back into the coaxial conductor from the boundary between it and the dielectric material. Such a transformer can advantageously contain a space into which the dielectric packing of the coaxial conductor can expand.

According to yet another aspect, the invention includes methods of coupling radiation into biological material using the devices according to the invention.

According to yet another aspect, the invention consists in methods of coupling radiation into biological material using the devices according to the invention.

Further advantages and features of the invention will become apparent to readers skilled in the art upon consideration of the following description of embodiments of the invention, the embodiments being described by way of example only, and with reference to the accompanying figures in which.

Figure 1:
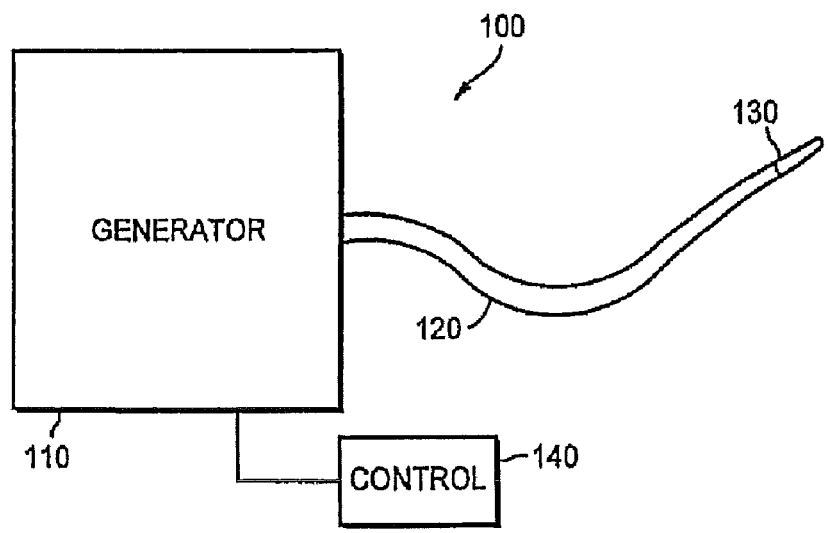
FIG. 1 is shows a first embodiment of the radiation applicator.

FIG. 1 shows the general arrangement of the radiation system 100. A radiation generator 110, for example, a microwave generator, produces radiation which is coupled into coaxial cable 120 which transmits the radiation to a distal tip region 130 at which there is an antenna for emitting the radiation into the material surrounding the tip 130. In use, the coaxial cable 120 is introduced into a living body and the tip 130 is positioned adjacent a region which it is desired to irradiate. For example, the device could be inserted into an artery to irradiate plaques on the walls thereof or the device could be introduced into a uterus to irradiate the endometrium. The supply of radiation is controlled by a control device 140, often a foot pedal, which is used to signal the microwave generator to begin, adjust or stop the supply of radiation to the tip 130.

Figure 2:
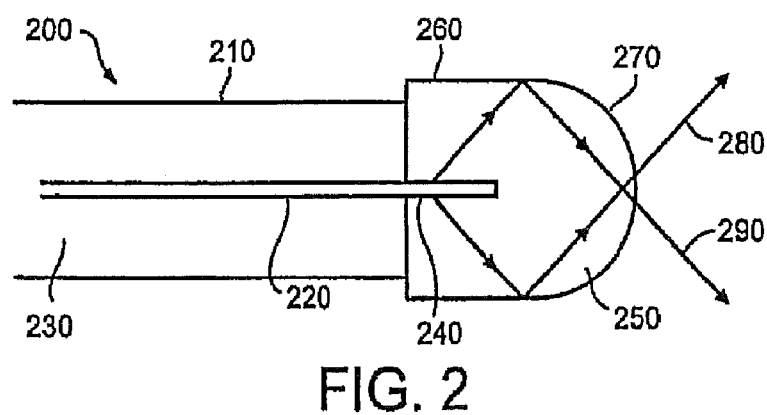
FIG. 2 is shows the tip section of the radiation applicator of FIG. 1 in more detail.

FIG. 2 shows the tip region 130 of the radiation applicator of FIG. 1 in more detail. The tip region, generally indicated 200, shows the distal end of the coaxial cable which comprises an outer conductor 210 spaced from a core conductor 220. The space between the conductors 210 and 220 is filled with dielectric material 230. The antenna for emitting radiation conducted by the cable comprises a length 240 of the core conductor of the coaxial cable extending beyond the outer conductor 210 at the distal end of the coaxial cable to form a monopole. To enhance the radiating qualities of the monopole 240, it is preferred that its length is about one half of a wavelength of the radiation dielectric. The monopole 240 is enveloped by dielectric body 250 in which the wavelength of the employed radiation is reduced below its free-space value hence enabling the monopole to be shorter than might otherwise be possible. The dielectric body 250 comprises a cylindrical portion 260 which envelops the monopole 240. The diameter of the cylindrical portion 260 is generally equal to the wavelength of the radiation in the dielectric at the operating frequency so that it is tuned to act as a resonator to increase the power it radiates. Also, the dielectric body comprises a hemispherical section 270 which supports partial internal reflection of the radiation from the antenna in the forward direction as indicated by arrows 280 and 290. Preferably, the hemispherical section 270 is dimensioned so as to provide a resonator which further enhances radiation from the dielectric body in 250 in the forward direction. Resonance of radiation partially reflected within the dielectric body 250 can be encouraged by, for example, dimensioning the hemispherical section 270 to have a radius approximately equal to one half of a wavelength of the radiation employed. It will be appreciated that the dielectric body can have other dimensions and shapes provided that they encourage forward propagation of the radiation by means of internal reflection and/or resonance.

When this equipment is to be used for endometrial ablation it is desirable to use radiation having a frequency around 9.2 GHz. In free-space, the wavelength of such radiation is about 32 mm. Forming the dielectric body from, for example, a material having a dielectric constant $\epsilon_R=25$ reduces the wavelength to about 6 mm. Correspondingly, the diameter and overall length of the dielectric body are then also about 6 mm.

Figure 3:
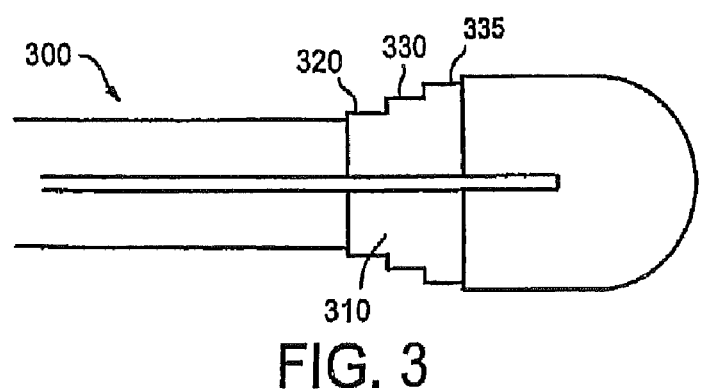
FIG. 3 shows a second embodiment of the tip section of the radiation applicator incorporating a transformer.

FIG. 3 shows an alternative embodiment of the tip section of the radiation applicator device, generally indicated 300. Here, in order to reduce reflection of radiation from the coaxial cable at the boundary between it and the dielectric body, a transformer 310 is incorporated between the coaxial cable and the dielectric body. The transformer 310 comprises several sections (for example, three: 320, 330, 340) of cylindrical shape and of successively increasing radius towards the dielectric body. Advantageously, at least the section 320 of the transformer adjacent the coaxial cable does not contain a solid filler material. This provides the benefit that, when the device is heated, for example in manufacture or in use, the dielectric material filling the space between the core and the outer conductors of the coaxial cable can expand into the transformer thus relieving otherwise deleterious pressures.

The near-field radiation generated by the applicator of FIGS. 2 and 3 extends from the monopole 240 a distance determined by the formula $2L^2/\lambda$, where L is the length of the monopole, and $\lambda$ is the wavelength of the radiation in the dielectric body 250. However, the preferred value of L is $\lambda/2$, and therefore the near-field radiation does not extend into the region of radius $\lambda/2$ about the monopole. Therefore, the near-field radiation does not extend into the more lossy biological material that surrounds the applicators in use, and the resulting detrimental affects of local charring and reduction of radiation penetration are reduced or avoided. Instead, the microwave power is emitted into the far-field to increase penetration and power transfer.

Figure 4:
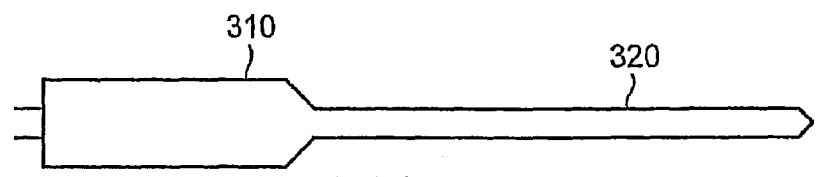
FIG. 4 shows a third embodiment of the radiation applicator.

FIG. 4 shows yet another embodiment of the invention in which a generator 310 supplies microwave energy via a rigid coaxial conductor 320 to a tip region at the distal end of the conductor. Dielectric packing 330 is provided between the inner and outer conductors of the coaxial conductor 320. As shown in more detail in FIG. 5, a length of the inner conductor 340 at the tip is exposed by removal of the outer conductor so as to form a monopole to emit radiation. The monopole 340 is embedded axially in a cylindrical body of dielectric 350 which has substantially the same outer diameter as the coaxial conductor 320. A pointed metal tip 370 is fixed to the end of the dielectric body 350 and serves to assist penetration into biological matter, such as a liver to perform ablation on a tumour. The monopole 340 preferably has a length substantially equal to half a wavelength of the radiation in the dielectric, and the radius of the dielectric body 350 is also preferably substantially equal to half a wavelength of the radiation in the dielectric. The near-field radiation emitted by the monopole will then lie within a region $2L^2/\lambda$, which is equal to a radius of half of the wavelength of the radiation in the dielectric so that the near-field lies substantially totally within the dielectric. The dielectric constant of the dielectric body is selected to be high so as reduce losses within the dielectric. The microwave energy is therefore emitted into the far-field region in an annular pattern around the tip so as to increase field penetration and power transfer. Typically, a radiation applicator used with a generator operating at 10 GHz and having a dielectric body with dielectric constant $\epsilon_R=25$, will have a dielectric body radius of 3 mm. Because the radius of the dielectric body 350 is substantially equal to half a wavelength, it is tuned to set as a resonator, which increases the power it radiates.

In order to reduce the diameter of the tip of the applicator, the dielectric body is made of a material with as high a dielectric constant as possible, except that this is limited by the dielectric constant of surrounding biological matter in which the applicator is used. When the dielectric constant of the dielectric body exceeds that of the biological matter, total internal reflection can occur at the outer surface of the dielectric body, and field penetration becomes evanescent and localized. In order to overcome this limitation, the dielectric body 350 may be formed with an inner core 360 composed of a material with a high dielectric constant, and an outer layer 380 composed of a dielectric with a lower dielectric constant intermediate that of the core and the surrounding biological material so as to match the wave impedance of the radiation between the core and the biological material. In order to achieve this, the refractive index of the outer layer 380 and that of biological material, and the outer layer thickness should be equal to a quarter of the wavelength of the radiation in the outer layer. Thus, the core radius would also be equal to a quarter of the wavelength of the radiation in the core in order to produce an overall nominal radius of half a wavelength at the tip.

In alternative embodiments of the invention, multiple outer layers may be used to increase the band-width of the applicator (i.e. the range of frequencies over which the applicator can be used) by making the layers each with a suitable refractive index and thickness. However, this will lead to an increase in the overall diameter of the tip. In the limit, the dielectric body could be made with continuously varying refractive index which decreases towards its outer surface.

Figure 6:
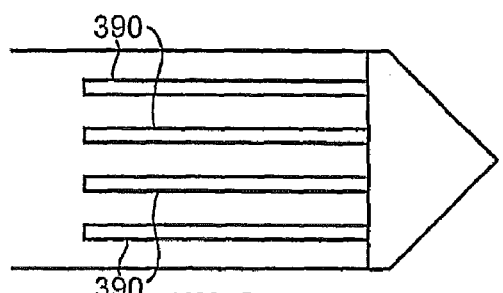
FIG. 6 shows a side-elevation of a variation design of the radiation applicator of FIG. 4.

An alternative technique to reduce the dielectric constant of the outer layer 380 comprises forming indentations such as grooves 390, shown in FIG. 6, in the outer surface so that the average dielectric constant of the dielectric and the material in the grooves is reduced. The grooves may run longitudinally or circumferentially around the body 350.

Figure 5:
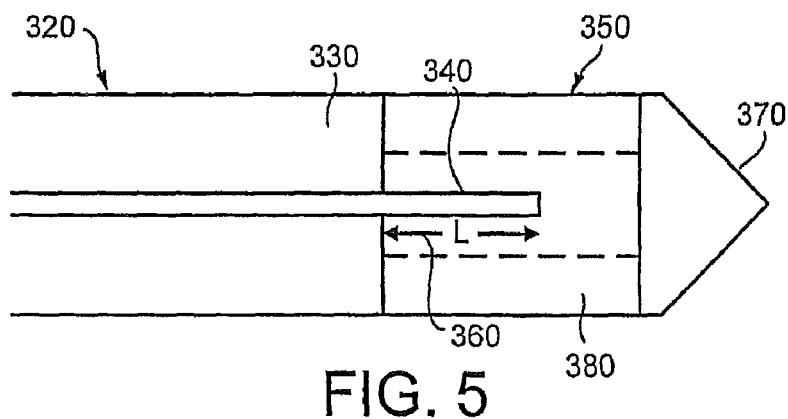
FIG. 5 shows the tip of the radiation applicator of FIG. 4.

It will be appreciated that the embodiment of FIGS. 2 and 3 can also be modified to incorporate an outer layer or layers of different dielectric constant, such as shown in FIGS. 5 and 6, the outer layer following the curve of the hemispherical tip.

Dielectric materials with a high dielectric constant that are suitable include those such as $TiO_2$ with permittivity of 100 and $CaTiO_2$ with permittivity of 155. These dielectrics would be suitable for use in the core 360 so as to reduce its diameter. The outer layer(s) 370 could be made of a composite of $TiO_2$ and $AlO_2$ having a permittivity between that of the core and the biological material. Materials with even higher permittivities may be used such as ferroelectric materials, an example being $Ba_{1-x}Sr_x TiO_3$ (BST) which has a permittivity of around 600.

Therefore, by suitable choice of dielectric(s) it is possible to produce radiation applicators with a tip diameter as low as 3 to 6 mm to allow their use in laparoscopic medical procedures, or even below 3 mm to allow percutaneous medical procedures.

Radiation applicators according to the invention can also be used to measure the dielectric constant of biological material by measuring the microwave radiation reflected back from the tip through the coaxial conductor.

The invention claimed is:

1. An elongate microwave radiator for insertion into a living body to treat tissue at a predetermined operating frequency, the radiator comprising a monopole antenna at its tip, the monopole antenna comprising:
    a monopole having a major dimension L; and
    a dielectric body surrounding the monopole, the dielectric body being configured to act as a resonator at the predetermined operating frequency and extending from the monopole a distance equal to at least $2L^2/\lambda$, where $\lambda$ is the wavelength of the radiation in the dielectric, so as to encompass substantially the whole of a near-field radiation emitted by the monopole, the dielectric body comprising a layer of dielectric material having a dielectric constant greater than or equal to 25.

2. The radiator as claimed in claim 1 in which the dielectric body extends from the monopole a distance equal to at least half the wavelength of the radiation in the dielectric.

* * * * *